United States Patent [19]

Lee et al.

[11] Patent Number: 4,592,370
[45] Date of Patent: Jun. 3, 1986

[54] EAR CANAL ELECTRODE FOR AUDITORY TESTING

[75] Inventors: John J. Lee, Cupertino; Arthur F. Avila, San Jose; Hal C. Danby, Palo Alto; Myron A. Beigler, Los Altos Hills, all of Calif.

[73] Assignee: Minnesota Mining and Manufacturing Company, St. Paul, Minn.

[21] Appl. No.: 444,624

[22] Filed: Nov. 26, 1982

Related U.S. Application Data

[63] Continuation-in-part of Ser. No. 424,353, Sep. 27, 1982, abandoned.

[51] Int. Cl.⁴ ............................................. A61B 5/12
[52] U.S. Cl. .................................... 128/746; 128/642
[58] Field of Search ............... 128/746, 642, 789, 784; 179/107 E; 181/129–130, 135; 339/253 R, 253 S, 256 RT

[56] References Cited

U.S. PATENT DOCUMENTS

| | | | |
|---|---|---|---|
| Re. 26,174 | 12/1961 | Leale | 179/107 E |
| Re. 29,487 | 12/1977 | Gardner | 128/152 |
| 521,800 | 6/1894 | Leech | 128/789 |
| 1,684,859 | 9/1928 | Catlin | 128/789 |
| 2,934,160 | 4/1960 | Touson | 181/130 |
| 3,303,902 | 2/1967 | Knott | 181/135 |
| 3,547,104 | 12/1970 | Buffington | 128/640 |
| 3,567,657 | 3/1971 | Lichtenstein | 128/639 |
| 3,783,201 | 1/1974 | Weiss | 179/107 E |
| 3,783,864 | 1/1974 | Moller | 128/152 |
| 3,882,848 | 5/1975 | Klar | 128/746 |
| 3,890,474 | 6/1975 | Glicksberg | 179/107 E |
| 3,935,401 | 1/1976 | Shore | 181/135 |
| 3,991,755 | 11/1976 | Vernon | 604/20 |
| 4,006,796 | 2/1977 | Coehorst | 181/130 |
| 4,088,133 | 5/1978 | Twentier | 128/644 |
| 4,109,648 | 8/1978 | Larke | 128/639 |
| 4,133,984 | 1/1979 | Akiyama | 179/107 E |
| 4,166,453 | 9/1979 | McClelland | 128/903 |

FOREIGN PATENT DOCUMENTS

| | | | |
|---|---|---|---|
| 197806 | 11/1976 | Fed. Rep. of Germany | 128/642 |
| 1263402 | 2/1972 | United Kingdom | 128/736 |
| 1423194 | 1/1976 | United Kingdom | 128/335 |

OTHER PUBLICATIONS

Lundborg, T. et al., *Scandanavian Auditory Supplementum No.* 13 (1981), pp. 55–64.
Erickson, D. et al., *Hearing Instruments* (1981), pp. 34–43.

*Primary Examiner*—Kyle L. Howell
*Assistant Examiner*—Francis J. Jaworski

[57] ABSTRACT

A non-invasive, external ear canal electrode and connector therefor useful for transmitting sound stimulus to an ear canal and for conducting electrical signals picked up from the ear canal epidermal surface. The electrode comprises an electro-conductive tube having resilient plastic foam elements attached to the end to be placed in the ear. One foam element is electro-conductive and impregnated with an electrolytically conductive medium, and the cells of the other sound absorbing elements are filled with air.

27 Claims, 8 Drawing Figures

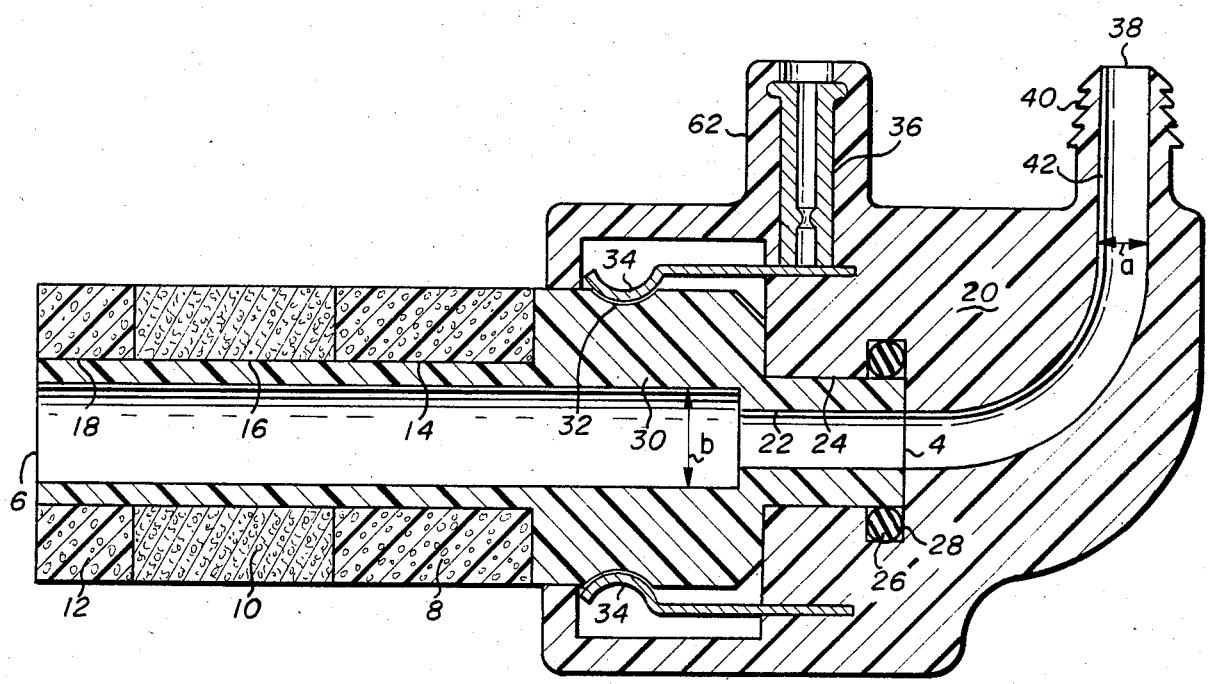
Fig_1
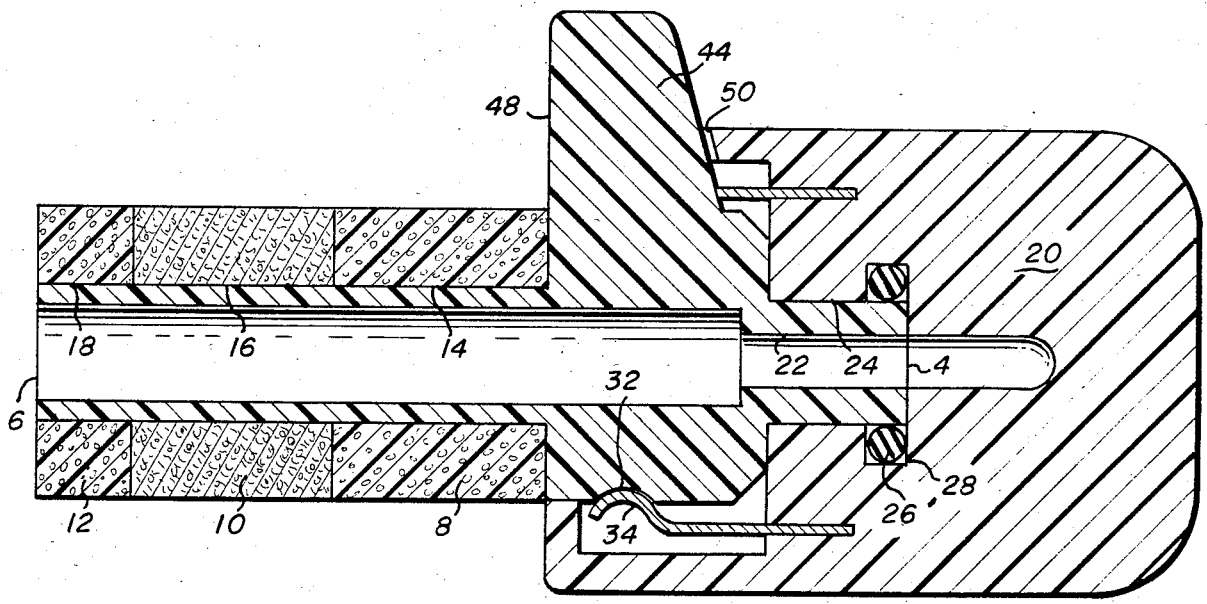
Fig_2

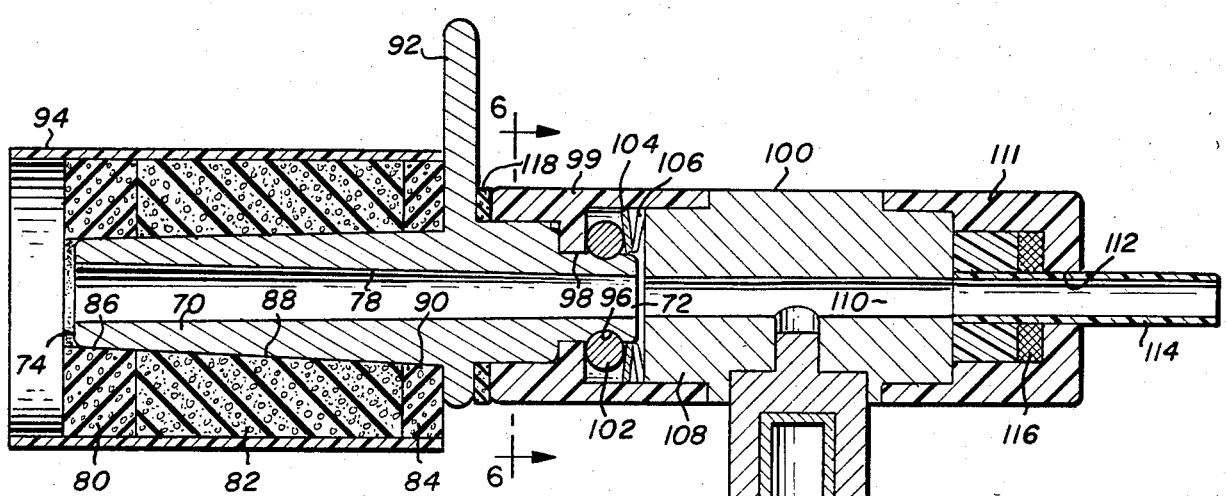
Fig_5
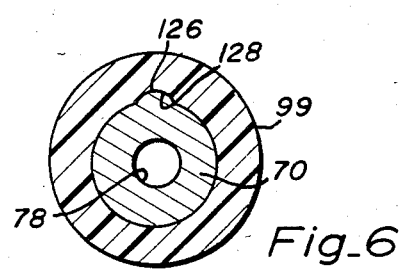
Fig_6
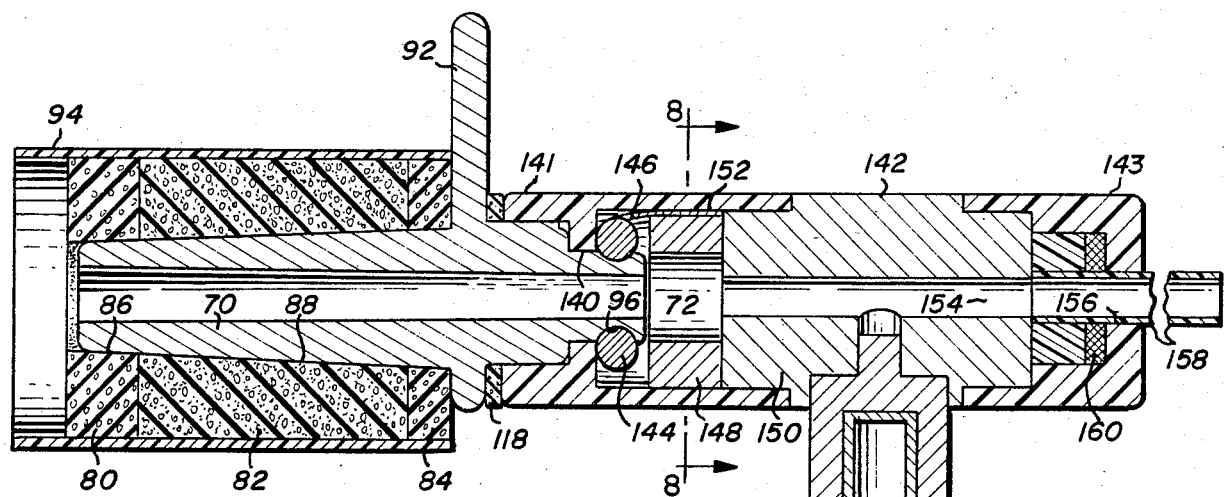
Fig_7
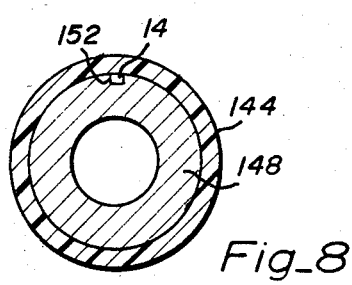
Fig_8

EAR CANAL ELECTRODE FOR AUDITORY TESTING

RELATIONSHIP TO COPENDING APPLICATIONS

This application is a continuation-in-part of application Ser. No. 424,353 filed Sept. 27, 1982, and now abandoned.

BACKGROUND OF THE INVENTION

1. Field of the Invention

Medical examinations to identify and diagnose hearing defects have historically involved physical examination of the ear canal and observing the subjective response to sound stimulus. Generally, the subjective sensitivity to volume has been routinely measured at several auditory frequencies. Most recently, the evoked action potentials resulting from auditory stimulation and auditory brainstem responses have been measured in an effort to identify more specifically the cause and degree of hearing loss and other hearing defects. Auditory brainstem response measurements involve auditory stimulation and measurement of the magnitude and response time of electrical signals originating from the otic nerve and brainstem in response to the auditory stimulus. The electrical signals are detected by using non-invasive electrodes mounted on the skin surface.

2. Description of the Prior Art

Ear canal mounted devices for providing auditory stimuli to the ear are well known in the art. The sound is frequently transmitted to the ear through a tubular component as shown in U.S. Pat. No. Re. 26,174 which is directed to a hearing aid and a method for its construction. In general, these devices are designed to provide a close or snug fit in the ear canal and may include resilient components to achieve this. U.S. Pat. No. 3,783,201 discloses a hearing aid with a flexible construction. U.S. Pat. No. 4,133,984 describes a hearing aid with a flexible, expandable (inflatable) end portion. These hearing aids are designed to provide auditory stimulus but are not suitable or intended to receive electrical signals from the surface of the ear canal.

Electrodes suitable for use in conducting electrical signals from the surface of the skin are commonly used in electrocardiology measurements and the like. These electrodes are designed to have a low resistance and high sensitivity as described in U.S. Pat. Nos. 3,547,104 and 4,166,453. The latter patent describes a body electrode comprising a porous foam disc impregnated with an electrically conductive gel and other components cooperating therewith made of electrically conductive plastic. These electrodes are designed to be easily applied to a flat skin surface. They are not suitable for ear canal insertion and are not adapted for providing any sound stimulus.

Conductive metal electrodes which penetrate the eardrum, i.e. transtympanic electrodes, have been used. They require use of an anesthetic, are painful and often result in infection. They have been used to pick up signals from close to the cochlea for increased signal strength of the first auditory action wave.

Typical electrodes designed for non-invasive external ear canal insertion for measuring auditory brainstem responses are described in *Scandanavian Audiology Supplementum No.* 13, titled "Scandanavian Symposium on Brain Stem" edited by T. Lundborg (Apr. 7-8, 1981). "Identification of Wave I by Means of Atraumatic Ear Canal Electrode" by Walter et al, pp 63-64 describes an electrode made of silver wire, the terminal end supporting a salt water impregnated cotton ball. "An Improved Technique for the Non-Invasive Recording of Brain-Stem Responses with a Specially Constructed Meatal Electrode" by Lang et al, pp 59-62 describe a silver wire electrode designed to be worn under earphones, the terminal end to be coated with electrode jelly. "Ear-canal Compared to Mastoid Electrode Placement in BRA" by Harder et al, pp 55-57 describes an acrylic plastic electrode with a silver element having a silver chloride surface layer embedded therein. Electrode paste is applied to the ear canal before inserting the electrode. These devices do not have the construction of the ear electrodes of this invention and do not provide the low resistance and high sensitivity thereof. Also, these devices have no means for providing auditory stimuli. In each referenced system, the auditory stimuli is provided through devices not physically associated with the ear electrode. An even greater limitation of all of the invasive and non-invasive electrodes of the prior art has been the requirement that a physician make the insertion because of the potential for inadvertent penetration of the eardrum.

OBJECTS AND SUMMARY OF THE INVENTION

It is an object of this invention to provide a noninvasive external ear canal electrode with decreased electrical resistance, greater electrical sensitivity, and greater sound acuity.

It is a further object of this invention to provide a safe, disposable ear canal electrode which can be simply and inexpensively manufactured and which can be easily and safely inserted by medical assistants with a minimum amount of training in ear anatomy without the risk of eardrum damage due to inadvertent penetration thereof.

In summary, the safe and non-invasive external ear canal electrode of this invention comprises a tubular electrode comprising electroconductive metal for conducting electrical signals picked up from the skin surface and for transmitting sound stimulus to the human ear canal surface. A resilient, open-celled, plastic foam member impregnated with an electrolytically conductive medium is mounted on the end of the tube which is to be placed in the ear canal, and it is designated to contact the epidermal skin surface of the ear canal and pick up and conduct electrical signals therefrom to the tube. A sound absorbing plastic foam is also mounted on the tube for reducing the level of environmental (background) noise reaching the ear drum. In the preferred embodiments of this invention, the tube is made of a silver, has a silver coating, or is a conductive silver filled plastic; the plastic foam members are annular elements surrounding the distal end of the tube; and the open-celled foam member impregnated with electrolytically conductive medium is positioned between two resilient annular members, at least the most proximal of which is a closed-cell resilient sound-absorbing plastic foam member.

BRIEF DESCRIPTION OF THE DRAWINGS

FIG. 1 is a cross-sectional side view of an ear canal electrode and connector of this invention with a sound adsorbing foam element.

FIG. 2 is a cross-sectional top view of the ear canal electrode and connector shown in FIG. 1.

FIG. 5 is a cross-sectional side view of another embodiment of the ear canal electrode of this invention.

FIG. 6 is a cross-sectional view of the embodiment shown in FIG. 5 taken along the line 6—6.

FIG. 7 is a cross-sectional side view of a still further embodiment of the ear canal electrode connector of this invention.

FIG. 8 is a cross-sectional view of the embodiment shown in FIG. 7 taken along the line 8—8.

DETAILED DESCRIPTION OF THE INVENTION

Figure 3:
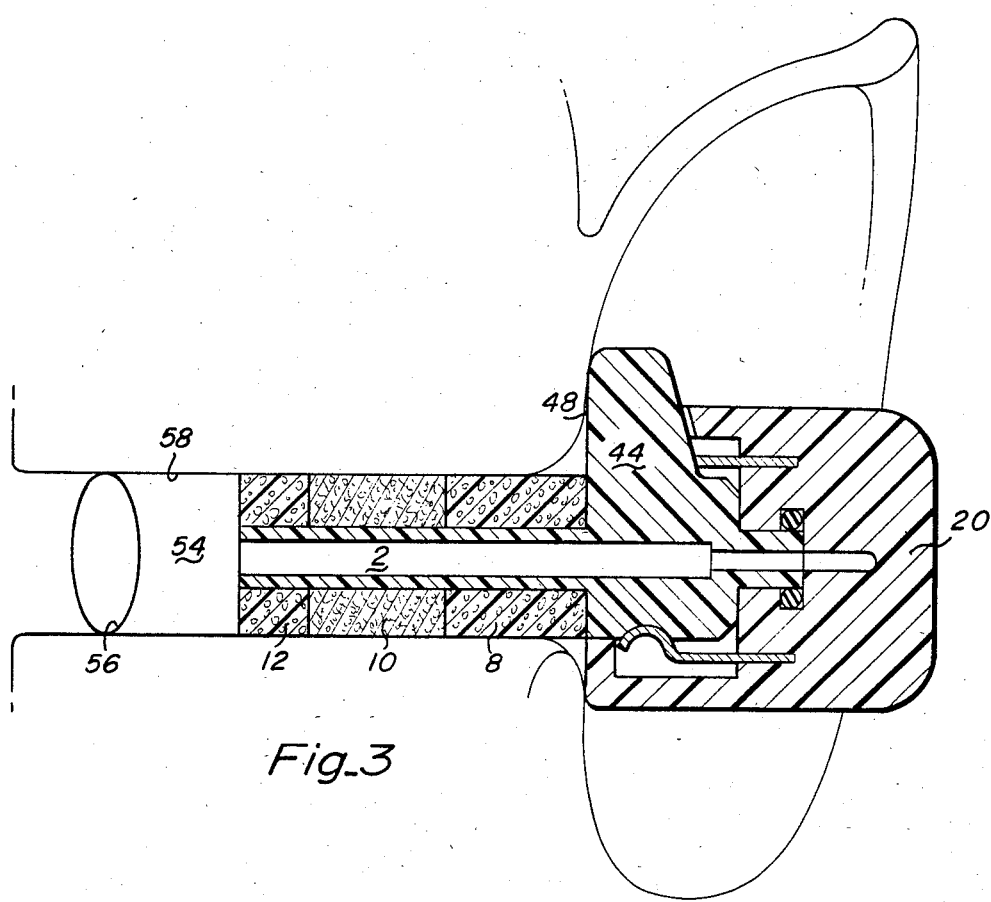
FIG. 3 is a cross-sectional top view of the ear canal electrode and connector of this invention in the final insertion position.

In an effort to diagnose the cause of partial and total hearing loss and other hearing defects, techniques have been developed around measurements of the auditory brainstem response (ABR) and electrocochleography (ECoG). The early techniques involved measuring electrical potential variations on the scalp surface within the first 10 milliseconds following auditory stimulation. The auditory system was stimulated with sound, usually in the form of short clicks or bursts of selected wave shape, amplitude and frequency. The resulting electrical field potentials generated by synoptic events and membrane potential fluctuations along the central auditory pathway, and in particular in the nerve cell layers of the deep brainstem structures, were transmitted through the volume (brain tissue, bone and extracellular fluid) of electrically conducting medium as potentials detected using the scalp electrodes. The amplitude and latency of the electrical potentials have been correlated with specific sites along the auditory nervous system pathway. Potentials originating from the cochlear transducer and auditory brainstem are the most significant. Irregularities in the amplitude and latency of the characteristic waves can be used to identify the degree and specific cause of a hearing deficiency.

A number of factors have limited the use of ABR and ECoG. Originally sharp clicks are distorted in passage and transmission in the ear passageways. The stimulus does not stimulate all of the cochlear hair cells simultaneously. Electrical potentials observed are very weak and often ambiguous due to distortion introduced by passage through the body structure and from background noise. Placements of electrodes in the ear canal and through the ear drum were found to reduce some distortion and give increased sensitivity. The surface of the ear canal is adjacent to dense, conductive bone, and electrical potentials measured on the ear canal surface have been transmitted through less insulative tissue and fluid. It was found that correctly designed metal, non-invasive ear canal surface electrodes can obtain signals equivalent to transtympanic electrodes. However, background noise was even greater in the ear with many non-invasive electrodes because of the configuration of the ear canal surface. Only with highly skilled investigators, elaborate skin surface preparation, expansion of the canal entrance with a speculum and insertion of electrodes with microsurgical forceps has resistance been measured below 10 Kohms.

The non-invasive external ear canal electrode of this invention, as set forth in more detail hereinafter, can be applied in a routine manner by ordinary, medically trained technicians to give an electrical resistance as low as one Kohm. This device also provides that sound is transmitted through an integral, acoustic horn with minimal distortion.

Referring to FIGS. 1 and 2, cross-sectional side and top views of the ear electrode and connector of this invention are shown. The tubular electrode 2 has a proximal end 4 and a distal end 6 and has a circular cross-section. The tubular electrode 2 can be of any electrically conducting, physiologically inert material which electrochemically reacts with the electrolytically conductive medium described hereinafter. It can be made of any electroconductive metal, for example aluminum, zinc, chromium, iron, cadmium, nickel, lead, lead-mercury amalgan, silver, copper, mercury, platinum, gold, or alloys thereof. The metal can be present as a coating around a metal or plastic tube or it can be an electroconductive filler dispersed in the plastic from which the tube is formed. The preferred metals are stainless steel, silver and silver alloys.

The plastic foam elements 8, 10 and 12 are preferably cylindrical with an outer diameter larger than the ear canal and with cylindrical passageways 14, 16 and 18, respectively, through which the tubular electrode 2 protrudes. The mutually contacting surfaces of the plastic foam elements 8, 10 and 12 are preferably bonded together to form a unitary laminated construction. The outer foam elements 8 and 12 are preferably bonded to the portions of the outer surface of the tube 2 which they contact to maintain their position during insertion of the device into the ear canal and its removal therefrom.

The function of the open-celled foam member 10 is to hold sufficient electrolytically conductive medium to provide an optimum electrical connection between the ear canal surface and the conductive surface of the tube 2.

The plastic foam member 10 can be made from any resilient, open-celled plastic foam material. It is preferably made from a continuously connecting cell material such as the very highly expanded product, FILTER FOAM made of polyurethane. The foam preferably contains or is impregnated with an electrolytically conductive medium which can be a liquid, gel, jelly, or other dispersion or suspension having good electroconductive properties and which electrochemically reacts with the conductive metal surface of the tubular electrode 2. For example, the electrolytically conductive medium can be an electrically conductive emulsion comprising an emulsified material dispersed in an aqueous solution of a conductive salt such as sodium chloride, potassium chloride or sodium sulfate and a surfactant dispersing agent. It can also be an electrically conducting jelly comprising an aqueous sodium chloride solution phase gelled with conventional gelling agents such as sodium carboxymethylcellulose and having as the conductive salt, potassium chloride, sodium sulfate, potassium sulfate, sodium bromide, potassium bromide, sodium nitrate, ammonium fluoride, ammonium bromide, ammonium nitrate, ammonium sulfate, and the like.

The plastic foam elements 8 and 12 have several functions. Plastic foam element 8 absorbs environmental sound and prevents significant levels of ambient sound from reaching the ear drum. It also supports the open-celled foam member 10, preventing its displacement during insertion. Particularly if it is bonded to the foam member 10, the foam member 8 supports foam member 10 from excessive collapse during insertion and serves additionally as an outer container wall for the electrolytically conductive medium. The plastic foam element 12 provides all of the functions provided by the foam member 18, particularly if it is bonded to the foam element 10. Additionally, it protects the ear canal surface from abrasive contact with the distal end 6. Serving as a container wall, it also prevents excess electrolytically conductive medium from advancing in the ear canal beyond the tube 2 where it might obstruct the opening in the end 6 and reduce acuity of the auditory signals delivered therefrom.

The plastic foam elements 8 and 12 are expandable, resilient plastic foam materials and can have either a open-cell or closed cell construction. Preferably it is closed cell foam and has a soft, easily distorted texture which quickly returns to its original shape when distorting pressure is removed. Suitable foam materials include polyurethane foams, fine closed cell low density polyethylene foams, closed cell expanded polyvinyl chloride foams, and the like.

The distal end of the tubular electrode 2 is releasably enclosed within a connector housing 20 which combines auditory signal and electrical connections. The distal end 4 of the tubular electrode has a terminal position 22 with a reduced inner and outer diameter which is received in a housing recess 24. Seal 26, which can be an elastomeric O-ring is retained in annular connector housing channel 28, bears against the outer surface of the terminal portion 22 in compressive, sealing engagement. Seal 26 prevents escape of air from the auditory passageway and resulting loss in auditory signal acuity. The intermediate portion 30 of the tubular electrode 2 has an annular recess 32 which engages the biased annular ring of conductive metal spring or tang elements 34. This both retains the tubular electrode within the connector housing and provides a secure, noise-free electrical connection between outer surface of the tubular electrode and the auditory brainstem signal jack 36 which is electrically connected to the spring elements 34.

The auditory signal connector 38 has serrated annular ridges 40 to sealingly engage the inner wall surface of flexible plastic tubing through which the auditory signal is transmitted. The inner diameter a of the auditory signal channel 42 enlarges to a diameter b in the tubular electrode 2 to provide a stepped horn configuration. This preserves auditory signal acuity.

Referring to FIG. 2, the safety stop 44 is shown. The safety stop is preferably a plastic component integral with the tubular electrode 2. The surface 48 abuts the external ear surface during insertion as is described in greater detail hereinafter with regard to FIGS. 3 and 4. The safety stop 44 projects beyond the outer surface of the connector 20 and is received within a keying slot 50 of the connector to maintain the desired respective alignment of the safety stop 44 and connector elements 36 and 38.

The tubular electrode and connector have been shown in the configuration suitable for insertion in the right ear of the patient. Orienting the safety stop 44 and receiving connector housing slot 50 in a position opposite that shown in FIG. 2, yields an ear canal electrode and connector suitable for use in the left ear, and both left and right ear configuration are intended.

The connector housing 20 and safety stop 44 are made of organic plastic polymer, preferably a thermoplastic organic polymer which can be injection or compression molded.

Referring to FIG. 3, a cross-sectional top view of the ear canal electrode and connector of this invention in the inserted operational position is shown. The safety stop surface 48 abuts the external ear surface behind the ear canal limiting the depth of penetration of the device in the ear canal 54 during insertion, and thereby preventing contact with eardrum 56. The plastic foam members 8, 10 and 12 positively engage the ear canal epidermal surface 58. The electrolytically conductive medium in the foam element 10 coats the epidermal surface 58 and insures good electrical contact between the skin surface and the surface of the electrode 2. This provides a minimal electrical resistance. An excess can be applied to the ear surface before the electrode is inserted. However, the plastic foam member 10 is preferably impregnated with a sufficient amount of the medium.

Because the safety stop 44 limits the distance of movement of the tubular electrode 2, risk of inadvertent contact or penetration of the eardrum 56 is completely eliminated, making routine insertion possible by ordinary medical testing assistants without specialized training.

Figure 4:
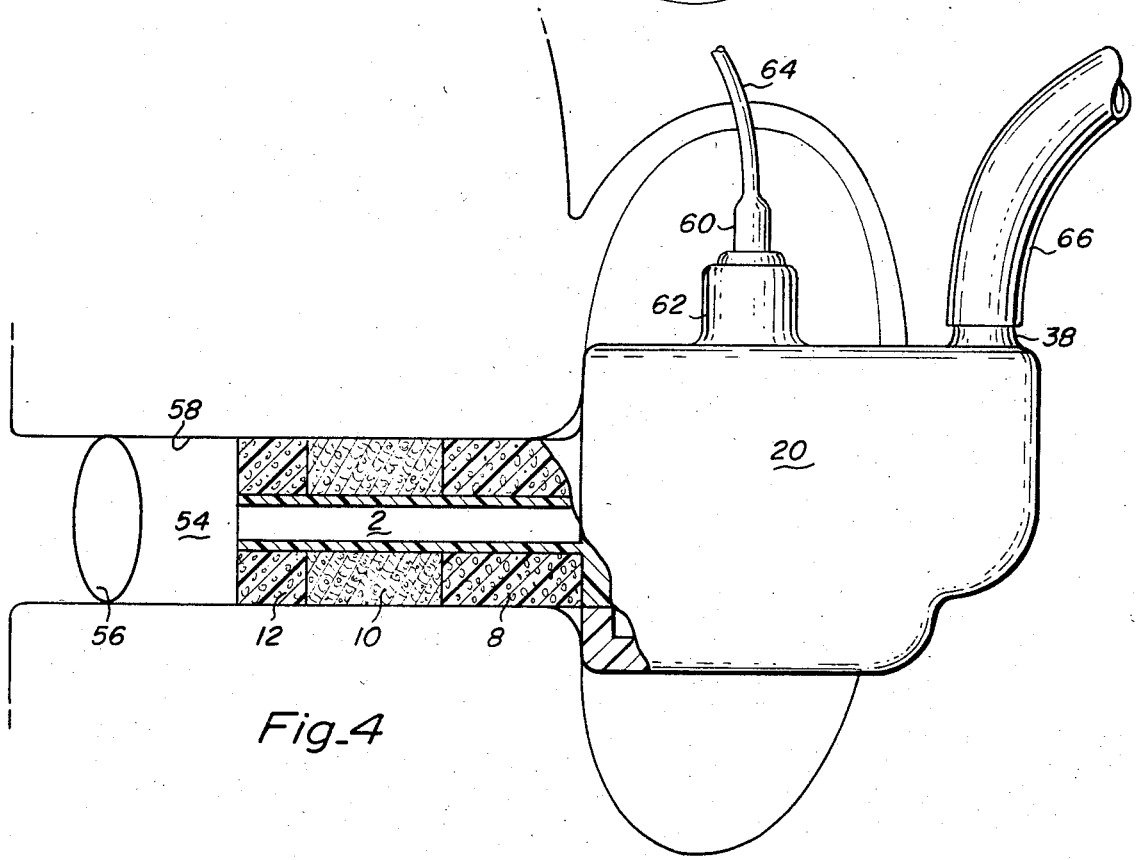
FIG. 4 is a partial cross-sectional side view of the device shown in FIG. 3.

Referring to FIG. 4, a partial cross-sectional side view of ear canal electrode and connector in the inserted, operational position is shown. An insulated plug or pin 60 engages the jack 36 (shown in FIG. 1) enclosed within the jack insulation 62. The insulated wire lead 64 connects the plug with an auditory brainstem signal analyzer (not shown). An auditor signal tubing 66 engages the auditory signal connector 38 and connects it with an auditory signal generator (not shown).

Referring to FIG. 5, a cross-sectional side view of a preferred embodiment of the ear electrode and connector of this invention is shown. The tubular electrode 70 has a proximal end 72 and a distal end 74 and has a circular cross-section. The tubular electrode 70 is a electrically conductive, physiologically inert material which electrochemically reacts with the electrolytically conductive medium as described hereinabove with respect to FIG. 1. The outer surface 76 has a configuration that is preferably frustuconical, tapering from a maximum outer diameter adjacent the proximal end 72 to a minimum outer diameter at the distal end 74. The inner surface 78 forms a horn having a minimum inner diameter at the proximal end 72 diverging to a maximum inner diameter at the distal end 74.

The plastic foam elements 80, 82 and 84 are preferably cylindrical with an outer diameter larger than the ear canal and with respective tapered frustuconical passageways 86, 88 and 90, respectively, through which the tubular electrode 70 protrudes. The mutually contacting surfaces of the plastic foam elements 80, 82 and 84 are preferably bonded together to form a unitary laminated construction. The outer foam elements 80 and 84 are preferably bonded to the portions of the outer surface of the tube 70 which they contact to maintain their position during insertion of the device into the ear canal and its removal therefrom. The taper of the outer surface of the tube 70 also performs this function.

The function of the open-celled foam member 82 is to hold sufficient electrolytically conductive medium to provide an optimum electrical connection between the ear canal surface and the conductive outer surface of the tube 70.

The plastic foam member 82 can be made from any resilient, open-celled plastic foam material such as Reticulated Foam (SCOTT) or FILTER FOAM made of polyurethane. The foam preferably contains or is impregnated with an electrolytically conductive medium as described above with respect to FIG. 1.

The plastic foam elements 80 and 84 have the composition and function described above with respect to the corresponding foam elements 8 and 12 in FIG. 1. A safety stop 92 is provided integral with the tubular electrode 70 to limit depth of insertion in the ear canal to a distance short of the eardrum, the safety stop abutting the external ear surface when insertion to the desired depth is effected. An outer tube 94 encloses the foam members 80, 82 and 84 to prevent damage and gel displacement during handling and storage, and can be made of coated paper or plastic.

The distal end 72 of the tubular electrode 70 has a reduced diameter and an annular recess 96 in the outer surface thereof. The distal end 72 releasably engages a matching cylindrical female cavity 98 in cap 99 of the connector 100. An annular conductive metal garter spring element 102 releasably engages the annular recess 96 when the electrode 70 is inserted in the cavity 98. Annular conductive metal washers 104 and 106 are placed under resilient pressure when the electrode 70 is inserted, the resulting spring pressure exerted by the washers maintaining secure electrical contact between the outer conductive surface of the recess 96, the garter spring 102 and the conductive connector hub 108 of the connector 100. Washer 104, a belleville washer having a slightly frustuconical shape, is placed with the base portion enclosing the surface of the garter spring 102. Washer 106, having a curved cross-section (a curved washer) is placed with face opposite the locus of the curve abutting the washer 104. Both washers 104 and 106 are made of conductive, spring metal.

The connector 100 has an audiosignal tubing passage 110 communicating with an inlet portion 112 of the cap 111 adapted to receive plastic or metal tubing 114 in secure engagement. Felt member 116 compressively and sealingly engages the outer surface of the tubing 114, preventing air loss therebetween. The passageway 110 provides unobstructed communication of the end of the tubing 114 and the proximal end 72 of the sound horn formed by the tubular electrode 70. Annular foam sealing ring 118 provides a further air seal between the cap 99 and electrode 70, preventing escape of air therebetween. Air leakage from the audiosignal passageway results in distortion of the audiosignal. The hub 108 also is conductively joined to the cambion jack portion 120 of the electrical signal connector 122.

Referring to FIG. 6, a cross-sectional view taken along the line 6—6 in FIG. 5 is shown to illustrate how proper alignment of the ear canal electrode 70 and connector cap 99 is insured. The proximal portion of the electrode 70 is provided with a spine 126 which engages a corresponding groove 128 in the sidewall of the female recess of the connector cap 99, permitting full engagement only if the elements are correctly aligned.

Referring to FIG. 7, a cross-sectional side view of a still further embodiment of the ear canal electrode connector of this invention is shown, the ear canal electrode being identical to that shown in FIG. 5.

The distal end 72 of the tubular electrode 70 has a reduced diameter and an annular recess 96. The distal end 72 releasably engages a matching cylindrical female cavity 140 in the cap 141 of the connector 142. An annular conductive metal garter spring element 144 releasably engages the annular recess 96 when the electrode 70 is inserted in the cavity 140. The garter spring element 144 has a conductive metal tang 146 welded thereto. Conductive spring retainer 148, in secure conductive contact with the metal hub 150 of the connector 142, has a groove 152 which receives the end of the tang 146 in a crimping or other secure conductive engagement.

FIG. 8, a cross-sectional view taken along line 8—8 in FIG. 7 shows the spring retainer groove 152 and tang 146 in greater detail.

The garter spring 144, forms a secure conductive contact with the outer conductive surface of the annular recess 96, and the tang 146 insures that a good conductive path is maintained from the garter spring 144, to the hub 150.

The connector 142 has an audiosignal tubing passage 154 communicating with an inlet portion 156 in cap 143 adapted to receive plastic or metal tubing 158 in secure engagement. Felt member 160 compressively and sealingly engages the outer surface of the tubing 158, preventing air loss therebetween. The passageway 154 provides unobstructed communication of the end of the tubing 158 and the proximal end 72 of the sound horn formed by the tubular electrode 70. The hub 150 also is conductively joined to the cambion jack portion 162 of the electrical signal connector 164.

The auditory signal generator and its associated magnetic field shielding can be of any standard type suitable for providing the auditory stimulation required for auditory brainstem response. The auditory sound generator is of standard construction well known in the art and is not an essential part of this invention.

A description of the procedures for measuring and analyzing auditory brainstem response is provided by "Physiological Mechanisms and Auditory Brainstem Evoked Response" by E. Borg, pp. 11–22 in the *Scandanavian Audiology Supplementum No. 13*, supra, and "Auditory Evoked Potential Instrumentation: How to Choose", by Erickson et al, *Hearing Instruments*, Volume 32, No. 8, 1981, pp. 31–43, the entire contents of which are incorporated by reference. Included in the latter article is a description of the equipment currently available for making auditory brainstem response test analysis and ancillary equipment such as auditory signal generators.

The growing interest in the auditory, evoked potential testing can be traced to the discovery of the auditory brainstem response recorded non-invasively from the human scalp. Subsequent research developed this test to provide a useful and versatile technique for evaluating hearing. It provides a means for examining patients who are difficult to test by behavioral means, efficiently discriminating between conductive and cochlear hearing disorders and differentiating peripheral and central pathology. Cochlear potentials of elevated magnitude indicate pressure in the inner ear. In some cases it can also reveal clinically asymptomatic lesions of the central pathways. The principal limitations derive from the high noise level in the electrical signal received from the skin surface. This noise level constitutes a serious impediment to full development of this testing means. Since the electrical signal being detected is less than one microvolt in amplitude, resistance or noise introduced at any point in the system causes a lower signal to noise ratio, seriously limiting the sensitivity of the device. Resistance introduced at the skin-electrode interface is very critical. To minimize this resistance, the conducting surface area in contact with the skin is maximized. Furthermore, the selection of sensor metal and electrolytically conductive medium is important.

The plastic foam elements provide a major improvement in the measurement of hearing response to sound generation. The foam elements 8 and 12 in the embodiment of FIG. 1, for example, reduce the level of background, environmental noise level against which the auditory sound signal transmitted to the ear canal is contrasted. This provides an effectively improved definition in the auditory sound signal as experienced by the ear drum. The ear electrode of this invention also provides as greatly reduced skin-ear surface resistance and far greater sensitivity. To minimize electrical resistance and impedance, it is important to employ an electrolytically conductive gel impregnated plastic foam. The gel provides an optimum conduction between the skin surface 58 and the conductive tubular electrode 2. The normal operating resistance has thus been reduced below 2 Kohm. As a result the signals received by the analyzer is of far greater quality than those previously obtained, permitting not only threshold hearing disorder screen testing but also a quantification of the extent of hearing loss as a function of selected sound frequencies.

A high degree of safety and ease of insertion has been achieved. Risk of eardrum penetration has been eliminated even when the electrode is inserted by medical assistants with no special training in ear anatomy. The special guards 44 and 92 limit insertion distance to a depth short of the eardrum.

We claim:

1. A non-invasive, external ear canal electrode comprising an electroconductive tubular electrode means having conductive metal on at least its surface for conducting electrical signals picked up from the ear canal surface and for transmitting a sound stimulus to an ear canal, said electrode means having a proximal end and a distal end, the distal end having foam means mounted thereon, the foam means including a resilient plastic open-celled foam means impregnated with an electrolytically conductive medium for contacting the skin surface of the ear canal and picking up and conducting electrical signals therefrom and a sound absorbing plastic foam means for reducing the level of environmental noise in the ear canal.

2. The ear canal electrode of claim 1 wherein said conductive metal comprises silver or stainless steel.

3. The ear canal electrode of claim 2 wherein said conductive metal comprises silver.

4. The ear canal electrode of claim 1 wherein the plastic foam means are annular plastic foam members surrounding said distal end.

5. The ear canal electrode of claim 4 wherein the sound absorbing plastic foam means is a closed cell, resilient plastic foam member.

6. The ear canal electrode of claim 5 wherein the plastic foam member impregnated with electrolytically conductive medium is an annular member positioned between two outer annular closed cell, resilient plastic foam members, at least one of said closed cell members constituting said sound absorbing plastic foam means.

7. The ear canal electrode of claim 6 wherein the two sound absorbing outer plastic foam members are laminated to the open-cell foam member and comprise a means for restraining electrolytically conductive medium movement form the open-celled foam member during insertion of the electrode into an ear canal.

8. The ear canal electrode of claim 1 wherein the proximal end of the electrode means has an annular recess means for engaging a retaining, electroconductive metal spring means in a connector housing.

9. The ear canal electrode of claim 1 including stop means projecting therefrom for abutting the external ear surface during insertion and limiting the depth of penetration of the distal end to a distance short of the ear drum.

10. An auditory testing device comprising tubular electrode means having a distal end for insert into an ear canal, resilient plastic foam on the distal end thereof, and a stop means projecting from the tubular electrode means for abutting the external ear surface during insertion and limiting the depth of penetration of the distal end to a distance short of the ear drum, wherein the resilient plastic foam includes a closed cell foam sound absorbing means.

11. The auditory testing device of claim 10 wherein the tubular means comprises a metal conductor, and the resilient plastic foam includes an open-cell foam element impregnated with electrolytically conductive medium.

12. An ear canal electrode in combination with a connector means, the ear canal electrode comprising a tube having an annular recess means on the outer surface thereof for releasably engaging a retention spring means of the connector means, the connector means having an electrode receiving recess means for receiving the electrode and retention spring means associated therewith for releasably engaging the annular recess means, wherein the connector means has an auditory signal transmitting passageway for communicating with the inner pasageway of the electrode tube.

13. The ear canal electrode of claim 12 wherein the retention spring means is conductively connected with a jack means for transmitting electrical signals to a signal analyzer.

14. The ear canal electrode of claim 12 including sealing means in said electrode receiving recess means for sealed engagement with the outer surface of the electrode tube.

15. The ear canal electrode of claim 14 wherein the retention spring means is conductively connected with a jack means for transmitting electrical signals to a signal analyzer.

16. An ear canal electrode in combination with a connector means, the ear canal electrode comprising a tube having an annular recess means on the outer surface thereof for releasably engaging a retention spring means of the connector, the connector means having a recess means for receiving the electrode and retention spring means associated therewith for releasably engaging the annular recess, wherein the tube has conductive metal on at least its surface for conducting electrical signals picked up from the ear canal surface and for transmitting a sound stimulus to an ear canal, said electrode means having a proximal end and a distal end, the distal end having foam means mounted thereon, the foam means including a resilient plastic open-celled form means impregnated with an electrolytically conductive medium for contacting the skin surface of the ear canal and picking up and conducting electrical signals therefrom and a sound absorbing plastic foam means for reducing the level of environmental noise in the ear canal.

17. The ear canal electrode of claim 16 wherein said conductive metal comprises silver or stainless steel.

18. The ear canal electrode of claim 17 wherein the plastic foam means are annular plastic foam members surrounding said distal end.

19. The ear canal electrode of claim 18 wherein the sound absorbing plastic foam member is a closed cell, resilient plastic foam.

20. The ear canal electrode of claim 19 wherein the plastic foam member impregnated with electrolytically conductive medium is an annular member positoned between two outer annular closed cell, resilient plastic foam members at least one of said closed cell members constituting said sound absorbing plastic foam means.

21. The ear canal electrode of claim 20 wherein the two sound absorbing outer plastic foam members are laminated to the open-cell foam member and comprise a means for restraining electrolytically conductive medium movement from the open-celled foam member during insertion of the electrode into an ear canal.

22. An ear canal electrode connector comprising a housing having an electrical connector means for connecting with a signal analyzer, an audio signal connector means including an auditory passageway for connecting with an audio signal generator, and a recess means for releasably engaging a tubular ear canal electrode, the recess means having an electrical contact means for establishing electrical contact with the ear canal electrode, the electrical contact means being connected to the electrical connector means, the recess means also having an audio signal opening positioned for alignment with the opening of said tubular electrode and communicating with the auditory passageway of the audio signal connector means.

23. The ear canal electrode connector of claim 22 wherein the electrical contact means is a metal spring means for releasably engaging a recess in the ear canal electrode.

24. The ear canal electrode connector of claim 23 wherein the housing includes a means for forming a sealing engagement with the tubular electrode to prevent escape of air from the junction formed by the recess means and the tubular electrode when the tubular electrode is engaged in the recess means.

25. The ear canal electrode connector of claim 23 wherein the metal spring means is an annular garter spring means.

26. The ear canal electrode connector of claim 25 including frustuconical and bent washer means positioned between the garter spring means and the electrical connector means for maintaining electrical contact therebetween.

27. The ear canal electrode connector of claim 25 wherein electrical contact between the garter spring means and the electrical connector means in maintained by a metal tang connecting the garter spring means and a spring retainer means in electrical contact with the electrical connector means.

* * * * *